United States Patent
Sun et al.

(10) Patent No.: US 12,193,870 B2
(45) Date of Patent: Jan. 14, 2025

(54) ELECTRONIC STETHOSCOPE

(71) Applicant: ScopeAround, Irvine, CA (US)

(72) Inventors: Yingjie Sun, Irvine, CA (US); Duo Ren, Irvine, CA (US)

(73) Assignee: ScopeAround, Irvine, CA (US)

( * ) Notice: Subject to any disclaimer, the term of this patent is extended or adjusted under 35 U.S.C. 154(b) by 177 days.

(21) Appl. No.: 18/190,772

(22) Filed: Mar. 27, 2023

(65) Prior Publication Data
US 2024/0298998 A1      Sep. 12, 2024

(30) Foreign Application Priority Data

Mar. 8, 2023   (CN) .......................... 202320494704.3

(51) Int. Cl.
| | | |
|---|---|---|
| A61B 7/04 | (2006.01) |
| H04R 1/02 | (2006.01) |
| H04R 1/46 | (2006.01) |
| H04R 3/00 | (2006.01) |
| H04R 17/02 | (2006.01) |

(52) U.S. Cl.
CPC ............... *A61B 7/04* (2013.01); *H04R 1/025* (2013.01); *H04R 1/46* (2013.01); *H04R 3/00* (2013.01); *H04R 17/02* (2013.01)

(58) Field of Classification Search
CPC . A61B 7/04; H04R 1/025; H04R 1/46; H04R 3/00; H04R 17/00
See application file for complete search history.

(56) References Cited

U.S. PATENT DOCUMENTS

| | | | |
|---|---|---|---|
| 4,940,023 A * | 7/1990 | Shue ................... | A61B 7/026 600/528 |
| 7,048,379 B2 | 5/2006 | Miller et al. | |
| 7,048,695 B1 | 5/2006 | Schwager | |
| 7,049,817 B2 | 5/2006 | Fleury et al. | |
| 2016/0252325 A1* | 9/2016 | Sammut .................. | F41G 3/08 42/122 |

FOREIGN PATENT DOCUMENTS

| | | | |
|---|---|---|---|
| CN | 106419952 A | | 2/2017 |
| CN | 111297393 A | * | 6/2020 |
| CN | 214208375 U | | 9/2021 |
| CN | 215534513 U | | 1/2022 |

OTHER PUBLICATIONS

Machine translation of CN111297393A (Year: 2020).*

* cited by examiner

*Primary Examiner* — Andrew Sniezek

(57) ABSTRACT

Discloses herein is an electronic stethoscope, including a connector, wherein a membrane type auscultation head is in threaded connection with one end of the connector, a piezoelectric sheet is fixedly mounted in the membrane type auscultation head, a grip is in threaded connection with the other end of the connector, a circuit board is clamped in the grip, the circuit board is electrically connected to the membrane type auscultation head, a storage battery is electrically connected to one side of the circuit board, the storage battery is clamped in the grip, a microswitch and a loudspeaker are mounted on the other side of the circuit board in an electrically connected manner, a main silicone key body is clamped in the grip, and the main silicone key body is attached to the microswitch.

6 Claims, 5 Drawing Sheets

ELECTRONIC STETHOSCOPE

TECHNICAL FIELD

The present invention relates to the technical field of stethoscopes, in particular to an electronic stethoscope.

BACKGROUND

A stethoscope is the most common diagnostic tool for a doctor and is generally composed of an auscultation head, a sound guide tube and an ear hook. The doctor attaches the auscultation head to a patient, sounds made by the heart, the lungs, arteries, veins and other internal organs of the patient are transmitted to the ear hook through the auscultation head and the sound guide tube, and the doctor listens to the sounds, made by the internal organs of the patient, by means of the ear hook, thereby achieving the auscultation purpose. However, at present, such common stethoscope completely depends on the doctor to listen and judge; the ear hook clamps ears of the doctor for a long time, resulting in pressing of the ears and discomfort, which affect the judgment of the doctor; in addition, the workload is large due to complete ear auscultation and analysis, and the voice frequency cannot be analyzed by a computer. In view of the above-mentioned problems, the inventor provides an electronic stethoscope to solve the above-mentioned problems.

SUMMARY

In order to solve the problems that at present, the common stethoscope completely depends on the doctor to listen and judge, the ear hook clamps ears of the doctor for a long time, resulting in pressing of the ears and discomfort, which affect the judgment of the doctor, the workload is large due to complete ear auscultation and analysis, and it is inconvenient to analyze the voice frequency by a computer, the present invention provides an electronic stethoscope.

In order to solve the above-mentioned technical problems, the present invention adopts the following technical solution: the electronic stethoscope, comprising a connector, wherein a membrane type auscultation head is in threaded connection with one end of the connector, a piezoelectric sheet is fixedly mounted in the membrane type auscultation head, a grip is in threaded connection with the other end of the connector, a circuit board is clamped in the grip, the circuit board is electrically connected to the membrane type auscultation head, a storage battery is electrically connected to one side of the circuit board, the storage battery is clamped in the grip, a microswitch and a loudspeaker are mounted on the other side of the circuit board in an electrically connected manner, a main silicone key body is clamped in the grip, and the main silicone key body is attached to the microswitch.

Preferably, the membrane type auscultation head is of a trumpet-shaped structure, a connection end is integrally formed on an outer wall of the small-diameter end of the membrane type auscultation head, the connection end is in threaded connection with the connector, an attachment end is integrally formed at the large-diameter end of the membrane type auscultation head, and the piezoelectric sheet is fixedly mounted on an inner wall of the attachment end.

Preferably, a threaded column is fixedly connected to one end of the connector, the threaded column is in threaded connection with the connection end, a threaded ring is fixedly arranged at the other end of the connector, the threaded ring is in threaded connection with the grip, and a microphone hole is formed in the connector and the threaded column.

Preferably, the grip comprises a housing, one end of the housing is sleeved on the threaded ring in a threaded manner, the circuit board, the main silicone key body and the storage battery are all clamped in an inner cavity of the housing, a key slot and loudspeaker holes are formed in an outer wall of one side of the housing, and the loudspeaker holes directly face the loudspeaker.

Preferably, an adjusting key of an elastic rubber structure and an on/off key are fixedly mounted on the main silicone key body, the adjusting key and the on/off key are clamped in the key slot, the adjusting key and the on/off key are attached to the microswitch, a loudspeaker through hole is formed in the main silicone key body, and the loudspeaker is clamped in the loudspeaker through hole.

Preferably, a type-c slot is formed in the end surface of the end of the housing that is far away from the connector, one end of a type-c sealing plug is fixedly connected to an inner wall of one side of the type-c slot, the type-c sealing plug is clamped in the type-c slot, a type-c interface is fixedly mounted at the end of the circuit board that is close to the type-c slot, the type-c interface is electrically connected to the circuit board, and the type-c sealing plug is closely attached to the type-c interface.

Compared with the prior art, the present invention has the beneficial effects as follows:

1. the housing and the connection end are connected to the threaded ring and the threaded column by means of threaded structures respectively, the microphone hole facilitates the electrical connection of the loudspeaker to the circuit board by means of a line, and the circuit board is clamped in the housing, thereby facilitating mounting and dismounting and facilitating connection;
2. the membrane type auscultation head is attached to the patient, the sounds cause vibration of the piezoelectric sheet so as to transmit the sounds to the membrane type auscultation head for collection, and sound signals are subjected to analog-to-digital conversion by means of the circuit board and then are sent out by the loudspeaker after being amplified proportionally, so that the doctor can listen to the sounds conveniently, the ear hook is prevented from pressing the ears of the doctor for a long time, and the comfort is improved; in addition, the proportionally amplified sounds sent out by the loudspeaker can be conveniently recorded by the computer for frequency analysis, thereby improving the auscultation efficiency and accuracy.

BRIEF DESCRIPTION OF THE DRAWINGS

Drawings constituting a portion of the present application are used to provide a further understanding to the present invention; and a schematic embodiment of the present invention and its description are intended for explaining the present invention, and should not be construed to unduly limit this invention. In the drawings.

Figure 1:
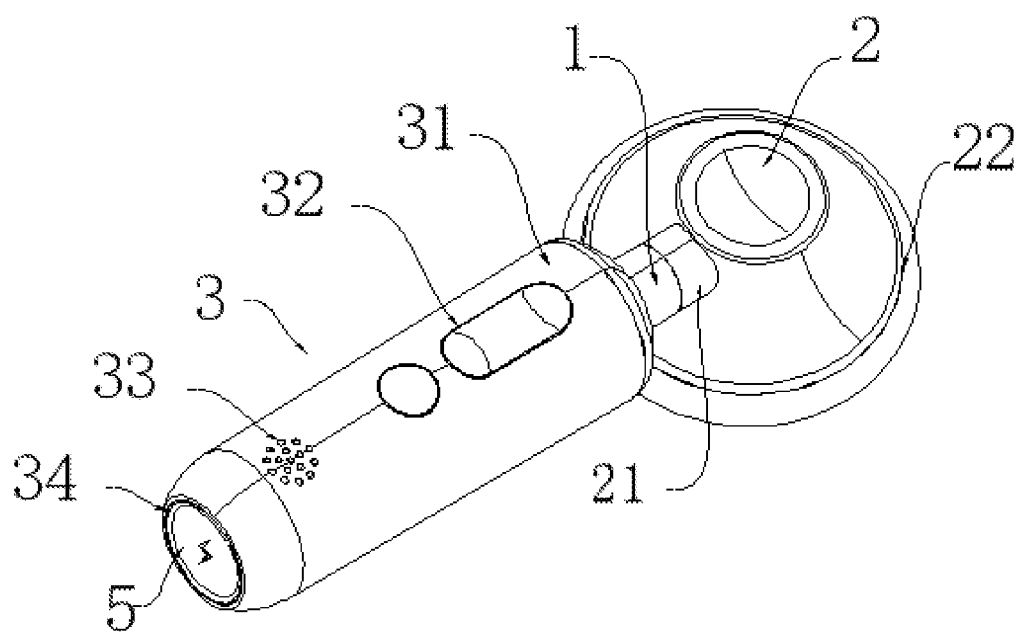
FIG. 1 is a structure diagram of the present invention.

Description of reference numerals: 1. connector; 2. membrane type auscultation head; 21. connection end; 22. attachment end; 3. grip; 31. housing; 32. key slot; 33. loudspeaker hole; 34. type-c slot; 4. piezoelectric sheet; 5. type-c sealing plug; 6. storage battery; 7. circuit board; 71. microswitch; 72. loudspeaker; 8. main silicone key body; 9. adjusting key; 10. on/off key; 11. loudspeaker through hole; 12. type-c interface; 13. threaded ring; 14. threaded column; and 15. microphone hole.

DETAILED DESCRIPTION OF THE EMBODIMENTS

The present invention will be described in detail below with reference to the accompanying drawings and in conjunction with the embodiment. Various examples are provided in the interpretation manner of the present invention, and are not intended to limit the present invention. In fact, those skilled in the art will know that amendments and modifications may be made in the present invention without departing from the scope or the spirit of the present invention. For example, features shown or described as part of an embodiment may be used in another embodiment so as to produce another embodiment. Therefore, it is expected that the present invention includes such amendments and modifications within the scope of the appended claims and equivalents thereof.

In the descriptions of the present invention, the orientations or positional relationships indicated by the terms "longitudinal", "transverse", "upper", "lower", "front", "rear", "left", "right", "vertical", "horizontal", "top", "bottom" and the like are orientations or positional relationships based on the drawings, are only for the purpose of facilitating describing of the present invention, and do not indicate that the present invention must be constructed and operated in the specific orientations. Therefore, they cannot be understood as limitations on the present invention. The terms "connection", "connecting" and "arrangement" used in the present invention should be understood in a broad sense, for example, the connection may be fixed connection, and may also be detachable connection; the connection may be direct connection, and may also be indirect connection by means of intermediate components; the connection may be wired electrical connection and wireless electrical connection, and may also be wireless communication signal connection; and for those of ordinary skill in the art, the specific meanings of the above-mentioned terms can be understood according to the specific situations.

The accompanying drawings show one or more examples of the present invention. Numeral and letter marks are used in the detailed descriptions to refer to the features in the accompanying drawings. Similar or like marks in the accompanying drawings and the descriptions have been used to refer to similar or like parts of the present invention. As used herein, the terms "first", "second", "third" and the like are used interchangeably so as to distinguish one component from another, and are not intended to indicate the positions or the importance of the individual components.

Figure 2:
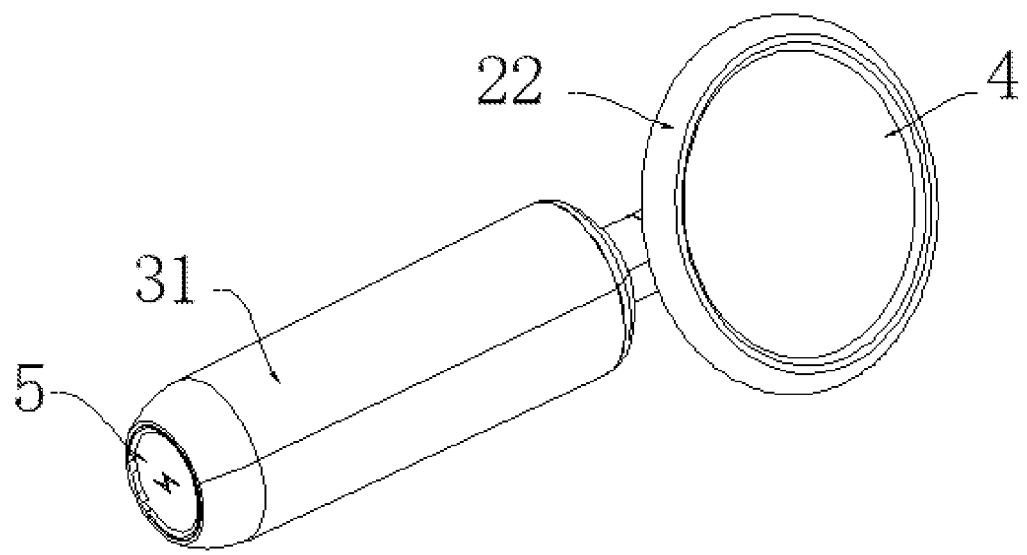
FIG. 2 is a structure diagram of a piezoelectric sheet of the present invention.
Figure 3:
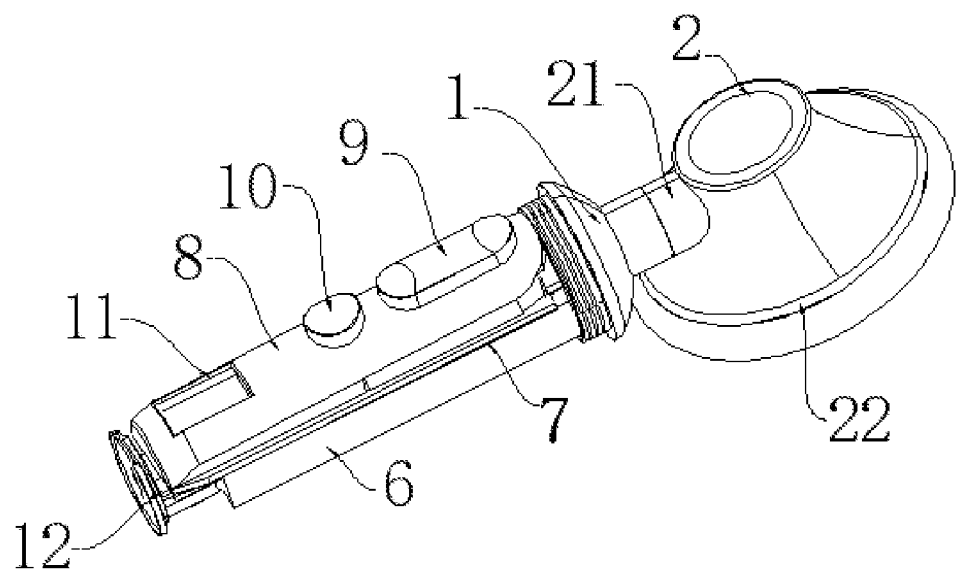
FIG. 3 is a structure diagram of a main silicone key body of the present invention.
Figure 4:
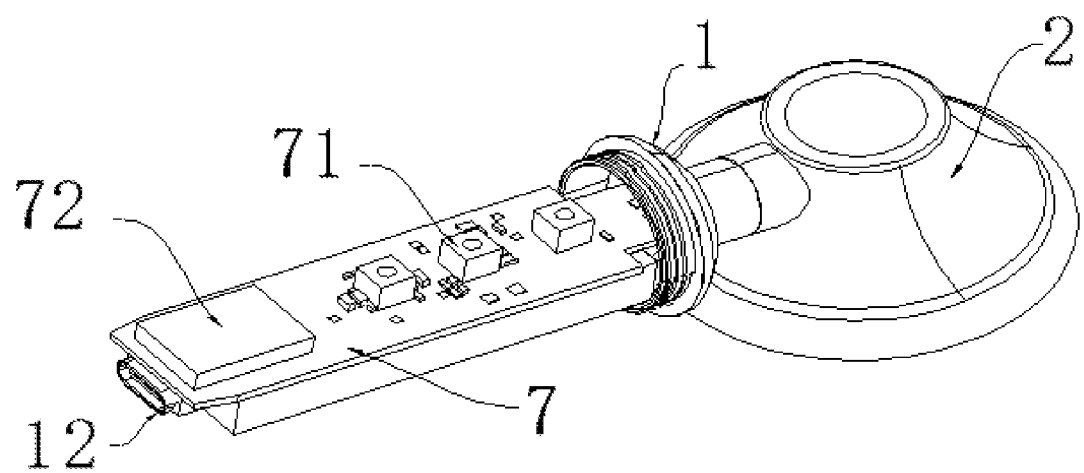
FIG. 4 is a structure diagram of a circuit board of the present invention.
Figure 5:
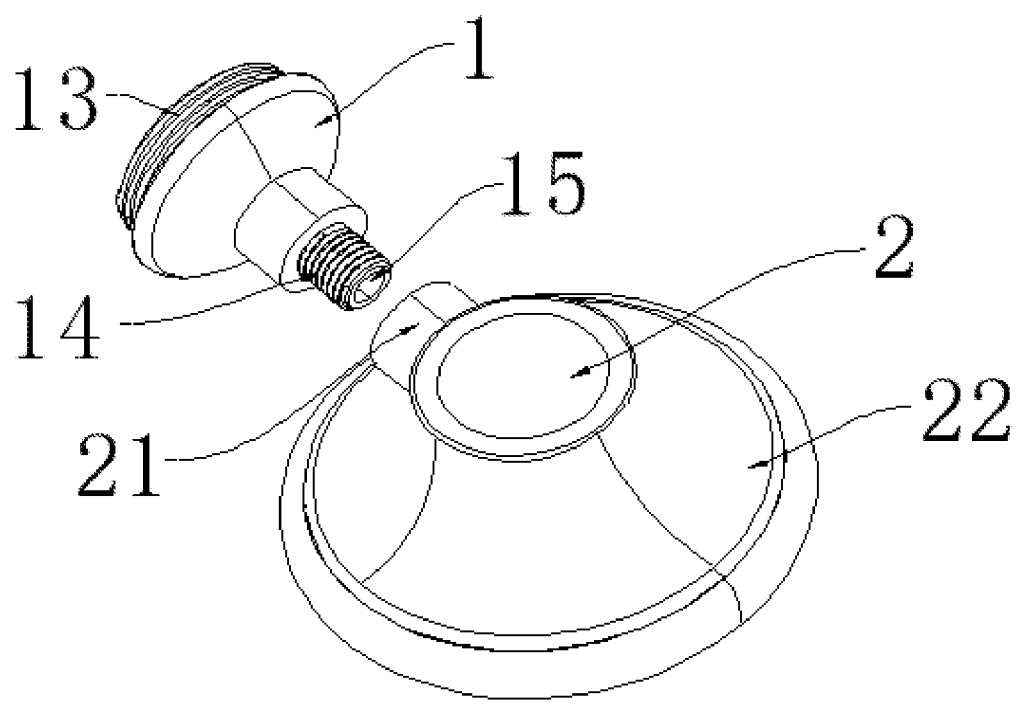
FIG. 5 is a structure diagram of a connector the present invention.

Embodiment: as shown in FIGS. 1-5, the present invention provides an electronic stethoscope, comprising a connector 1, wherein a membrane type auscultation head 2 is in threaded connection with one end of the connector 1, a piezoelectric sheet 4 is fixedly mounted in the membrane type auscultation head 2, a grip 3 is in threaded connection with the other end of the connector 1, a circuit board 7 is clamped in the grip 3, the circuit board 7 is electrically connected to the membrane type auscultation head 2, a storage battery 6 is electrically connected to one side of the circuit board 7, the storage battery 6 is clamped in the grip 3, a microswitch 71 and a loudspeaker 72 are mounted on the other side of the circuit board 7 in an electrically connected manner, a main silicone key body 8 is clamped in the grip 3, and the main silicone key body 8 is attached to the microswitch 71.

By means of the above-mentioned technical solution, the membrane type auscultation head 2 is attached to a patient, sounds cause vibration of the piezoelectric sheet 4 so as to transmit the sounds to the membrane type auscultation head 2 for collection, and sound signals are subjected to analog-to-digital conversion by means of the circuit board 7 and then are sent out by the loudspeaker 72 after being amplified proportionally, so that a doctor can listen to the sounds conveniently, an ear hook is prevented from pressing the ears of the doctor for a long time, and the comfort is improved; in addition, the proportionally amplified sounds sent out by the loudspeaker 72 can be conveniently recorded by a computer for frequency analysis, thereby improving the auscultation efficiency and accuracy.

Further, the membrane type auscultation head 2 is of a trumpet-shaped structure, a connection end 21 is integrally formed on an outer wall of the small-diameter end of the membrane type auscultation head 2, the connection end 21 is in threaded connection with the connector 1, an attachment end 22 is integrally formed at the large-diameter end of the membrane type auscultation head 2, and the piezoelectric sheet 4 is fixedly mounted on an inner wall of the attachment end 22; a threaded column 14 is fixedly connected to one end of the connector 1, the threaded column 14 is in threaded connection with the connection end 21, a threaded ring 13 is fixedly arranged at the other end of the connector 1, the threaded ring 13 is in threaded connection with the grip 3, and a microphone hole 15 is formed in the connector 1 and the threaded column 14; the grip 3 comprises a housing 31, one end of the housing 31 is sleeved on the threaded ring 13 in a threaded manner, the circuit board 7, the main silicone key body 8 and the storage battery 6 are all clamped in an inner cavity of the housing 31, a key slot 32 and loudspeaker holes 33 are formed in an outer wall of one side of the housing 31, and the loudspeaker holes 33 directly face the loudspeaker 72; an adjusting key 9 of an elastic rubber structure and an on/off key 10 are fixedly mounted on the main silicone key body 8, the adjusting key 9 and the on/off key 10 are clamped in the key slot 32, the adjusting key 9 and the on/off key 10 are attached to the microswitch 71, a loudspeaker through hole 11 is formed in the main silicone key body 8, and the loudspeaker 72 is clamped in the loudspeaker through hole 11.

By means of the above-mentioned technical solution, the housing 31 and the connection end 21 are connected to the threaded ring 13 and the threaded column 14 by means of threaded structures respectively, thereby facilitating mounting and dismounting and facilitating connection; the membrane type auscultation head has a layer of membrane which filters out low-frequency sounds with the frequency lower than 200 Hz, so that the membrane type auscultation head is more sensitive to high-frequency sounds; during usage, the membrane type auscultation head should be attached to the human body hard, the microphone hole 15 picks up the sounds, and the circuit board 7 is clamped in the housing 31; and during usage, a power supply is controlled by the on/off key 10 to be turned on and off, the microswitch 71 is pressed by the adjusting key 9 to control the amplification proportion of the sounds, thus the amplification of the sounds by the loudspeaker 72 is adjusted, and the auscultation by the doctor is facilitated.

Further, a signal amplification module, a noise reduction processing module, a Bluetooth drive module and a power module are designed on the circuit board 7 so as to realize analog-to-digital conversion amplification and noise reduction of the sound signals.

Further, a type-c slot 34 is formed in the end surface of the end of the housing 31 that is far away from the connector 1, one end of a type-c sealing plug 5 is fixedly connected to an inner wall of one side of the type-c slot 34, the type-c sealing plug 5 is clamped in the type-c slot 34, a type-c interface 12 is fixedly mounted at the end of the circuit board 7 that is close to the type-c slot 34, the type-c interface 12 is electrically connected to the circuit board 7, and the type-c sealing plug 5 is closely attached to the type-c interface 12.

By means of the above-mentioned technical solution, the type-c interface 12 can be conveniently externally connected to a charger to charge the storage battery 6; meanwhile, a data line can also be externally connected by means of the type-c interface 12 to directly transmit the sound signals to the computer, thereby avoiding the drying caused by secondary recording of the sounds by the computer, and improving the analysis accuracy of the computer; and the type-c sealing plug 5 is configured to perform dust protection on the type-c interface 12.

The working principle is as follows: the housing 31 and the connection end 21 are connected to the threaded ring 13 and the threaded column 14 by means of the threaded structures respectively, thereby facilitating mounting and dismounting and facilitating connection; the microphone hole 15 picks up the sounds, and the circuit board 7 is clamped in the housing 31; during usage, the membrane type auscultation head 2 is attached to the patient, the sounds cause the vibration of the piezoelectric sheet 4 so as to transmit the sounds to the membrane type auscultation head 2 for collection, and the sound signals are subjected to analog-to-digital conversion by means of the circuit board 7 and then are sent out by the loudspeaker 72 after being amplified proportionally, so that the doctor can listen to the sounds conveniently, the ear hook is prevented from pressing the ears of the doctor for a long time, and the comfort is improved; in addition, the proportionally amplified sounds sent out by the loudspeaker 72 can be conveniently recorded by the computer for frequency analysis, thereby improving the auscultation efficiency and accuracy.

Obviously, those skilled in the art can make various amendments and modifications to the present invention without departing from the spirit and the scope of the present invention. Therefore, if these amendments and modifications to the present invention fall within the scope of the claims of the present invention and the equivalent technologies thereof, the present invention is intended to include these amendments and modifications.

What is claimed is:

1. An electronic stethoscope, comprising a connector, wherein a membrane type auscultation head is in threaded connection with one end of the connector, a piezoelectric sheet is fixedly mounted in the membrane type auscultation head, a grip is in threaded connection with the other end of the connector, a circuit board is clamped in the grip, the circuit board is electrically connected to the membrane type auscultation head, a storage battery is electrically connected to one side of the circuit board, the storage battery is clamped in the grip, a microswitch and a loudspeaker are mounted on the other side of the circuit board in an electrically connected manner, a main silicone key body is clamped in the grip, and the main silicone key body is attached to the microswitch.

2. The electronic stethoscope according to claim 1, wherein the membrane type auscultation head is of a trumpet-shaped structure, a connection end is integrally formed on an outer wall of the small-diameter end of the membrane type auscultation head, the connection end is in threaded connection with the connector, an attachment end is integrally formed at the large-diameter end of the membrane type auscultation head, and the piezoelectric sheet is fixedly mounted on an inner wall of the attachment end.

3. The electronic stethoscope according to claim 2, wherein a threaded column is fixedly connected to one end of the connector, the threaded column is in threaded connection with the connection end, a threaded ring is fixedly arranged at the other end of the connector, the threaded ring is in threaded connection with the grip, and a microphone hole is formed in the connector and the threaded column.

4. The electronic stethoscope according to claim 3, wherein the grip comprises a housing, one end of the housing is sleeved on the threaded ring in a threaded manner, the circuit board, the main silicone key body and the storage battery are all clamped in an inner cavity of the housing, a key slot and loudspeaker holes are formed in an outer wall of one side of the housing, and the loudspeaker holes directly face the loudspeaker.

5. The electronic stethoscope according to claim 4, wherein an adjusting key of an elastic rubber structure and an on/off key are fixedly mounted on the main silicone key body, the adjusting key and the on/off key are clamped in the key slot, the adjusting key and the on/off key are attached to the microswitch, a loudspeaker through hole is formed in the main silicone key body, and the loudspeaker is clamped in the loudspeaker through hole.

6. The electronic stethoscope according to claim 4, wherein a type-c slot is formed in the end surface of the end of the housing that is far away from the connector, one end of a type-c sealing plug is fixedly connected to an inner wall of one side of the type-c slot, the type-c sealing plug is clamped in the type-c slot, a type-c interface is fixedly mounted at the end of the circuit board that is close to the type-c slot, the type-c interface is electrically connected to the circuit board, and the type-c sealing plug is closely attached to the type-c interface.

\* \* \* \* \*